United States Patent
Himmelsbach et al.

(10) Patent No.: US 6,812,170 B1
(45) Date of Patent: Nov. 2, 2004

(54) SUPPORT MATERIAL WITH A COHESIVE ADHESIVE SUBSTANCE

(75) Inventors: Peter Himmelsbach, Buxtehude (DE); Andreas B. Kummer, Hamburg (DE); Wolfgang Meyer-Ingold, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 10/009,147

(22) PCT Filed: May 3, 2000

(86) PCT No.: PCT/EP00/03939
§ 371 (c)(1),
(2), (4) Date: Jun. 3, 2002

(87) PCT Pub. No.: WO00/68334
PCT Pub. Date: Nov. 16, 2000

(30) Foreign Application Priority Data

May 11, 1999 (DE) ......................................... 199 21 743

(51) Int. Cl.⁷ .............................. C09J 7/04; A61L 15/58
(52) U.S. Cl. ....................... 442/149; 442/150; 428/343; 428/355 BL; 525/98
(58) Field of Search .............................. 442/150, 149; 428/343, 355 BL; 525/98, 99

(56) References Cited

U.S. PATENT DOCUMENTS 4,859,521 A * 8/1989 Pike et al. .................. 428/195
5,453,319 A * 9/1995 Gobran ........................ 428/355
2001/0051482 A1 * 12/2001 Himmelsbach et al. ..... 442/151

FOREIGN PATENT DOCUMENTS

EP 0826380 A2 * 3/1998
EP 0885942 A1 * 12/1998
WO WO97/43993 * 11/1997

OTHER PUBLICATIONS

EP0826380 Pat Abstract, Mar. 4, 1998.*

* cited by examiner

Primary Examiner—Daniel Zirker
(74) Attorney, Agent, or Firm—Norris McLaughlin & Marcus

(57) ABSTRACT

A backing material for medical use with a pressure-sensitively adhesive coating on at least one side, having an ultimate tensile stress strength of at least 800 cN/cm and a bond strength to the reverse of the backing of not less than 10 cN/cm, the latex-free, cold seal composition applied to the backing material comprising one or more block copolymers having a styrene content of less than 65% by weight and having a tan δ of less then 0.4 at a temperature of 25° C. and a frequency of 100 rad/s.

26 Claims, 2 Drawing Sheets

SUPPORT MATERIAL WITH A COHESIVE ADHESIVE SUBSTANCE

Figure 1:
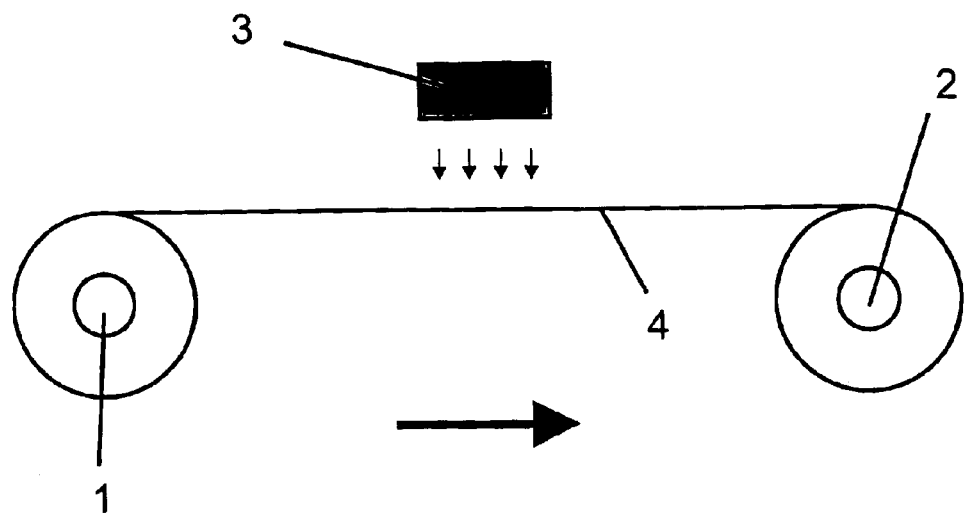

This application is a 371 of PCT/EP00/03939 filed on May 3, 2000.

The invention relates to a backing material coated on at least one side with a latex-free, cohesive adhesive—i.e., cold seal—composition for medical uses as for example bandages, dressings or dressing materials, in which the individual plies or turns of the dressing stick reliably only to themselves, with little or no sticking to other substrates, particularly the skin, hair or clothes.

Backing materials for medical use with a cohesive coating are known; they are available commercially under the name Elohaft® or Gazofix® from Beiersdorf. These products are normally made using a cold seal composition based on natural rubber.

For certain medical indications, sticking to the skin is not a necessity. In such cases it is advantageous if the product sticks only to itself and not to the skin, hair or clothing. These product properties promote painless, residueless removal of the bandage.

A disadvantage with these products, besides the limited light, temperature, and aging stability, is the presence of proteins and peptides, which can in some cases lead to allergies. Moreover, these systems are not processed as 100% systems, and it is therefore necessary to remove auxiliaries from the cold seal composition after it has been applied to the backing. Systems without a carrier matrix—that is, systems without common organic or inorganic solvents or dispersion media—are referred to as 100% systems. They are processed in the elastic or thermoplastic state. One common mode of processing is that of the melt.

DE U 86 24 190 describes a cohesive dressing material consisting of a backing material and a coating based on an acrylic resin dispersion. Disadvantageous features of this system include the poor shear properties and the removal of the auxiliary on application.

DE A 688 430 discloses a bandage which is impregnated with natural latex and undergoes an aftertreatment with acetic acid. Bandages of this kind, however, are disadvantageous in terms of their flexibility and textile resemblance. Further, this process is not advantageous owing to the additional workstep of aftertreatment.

U.S. Pat. No. 2,238,878 describes a dressing which is coated with a natural latex.

U.S. Pat. No. 3,575,782 discloses a method of producing elastic covering materials comprising nonwoven fibrous webs and highly elastic rubber or polyurethane yarns. The binders of the nonwoven material that are used give it a pressure-sensitively adhesive quality.

EP 0 885 942 A1 discloses an adhesive composition which has a high UV stability. For the blend, block copolymers based on SEPS diblock copolymers and SEBS triblock copolymers may be used. A cold seal composition is not described. The values for bond strength to skin and to the backing material, and the tack, show that cold seal adhesion is not achieved.

EP 0 443 263 discloses an adhesive composition possessing low tack. No description is given of its use for medical products.

A further adhesive dressing is described in DE-A 29 12 129, and is produced by ultrafine distribution of a rubber dispersion.

U.S. Pat. No. 5,692,937 describes a stretchable cohesive bandage coated with a polyurethane dispersion.

DE 196 31 422 discloses a backing material with a self-adhesive coating on at least one side, the self-adhesive composition being a pressure-sensitive hotmelt composition which at a frequency of 0.1 rad/s has a dynamic-complex glass transition temperature of less than −3° C., preferably from −6° C. to −30° C., with very particular preference from −9°C. to −25° C. According to the disclosure therein, the ratio of the loss modulus (viscous component) to the storage modulus (elastic component) of the pressure-sensitive hotmelt composition, at a frequency of 100 rad/s and 25° C., is greater than 0.7. With further preference, the ratio of the loss modulus (viscous component) to the storage modulus (elastic component) of the pressure-sensitive hotmelt composition, at a frequency of 0.1 rad/s and 25° C., is less than 0.40. Backings coated with an adhesive composition of this kind, however, do not exhibit cohesive properties. Instead, very high bond strengths are to be set when the bandage is bonded to the skin.

It is an object of the invention to produce a pressure-sensitively adhesively coated backing material which in particular is free from latex and natural rubber, which sticks only to itself, and which may be removed without residue from the skin.

The invention accordingly provides a backing material for medical use with a pressure-sensitively adhesive coating on at least one side, having an ultimate tensile stress strength of at least 800 cN/cm and a bond strength to the reverse of the backing of not less than 10 cN/cm, the latex-free, cold seal composition applied to the backing material comprising one or more block copolymers having a styrene content of less than 65% by weight and having a tan δ of less than 0.4 at a temperature of 25° C. and a frequency of 100 rad/s.

The high shear strength of the cold seal composition is achieved through the cohesive nature of the polymer.

The cold seal composition is preferably a hotmelt cold seal composition, which if desired may have been doped. The softening point of the hotmelt cold seal composition is higher than 50° C., since the coat application temperature is generally at least 70° C., preferably between 90° C. and 190° C., with very particular preference from 75° C. to 140° C. If desired, a postcrosslinking by means of UV or electron beam irradiation may be appropriate, depending on the specific structure of the parent polymer or its additives.

For systems which stick with particular strength, the cold seal composition is based preferably on A-B or A-B-A block copolymers or mixtures thereof. The hard phase A is principally polystyrene or its derivatives and the soft phase B is ethylene, propylene, butylene, butadiene, isoprene or mixtures thereof, with particular preference ethylene, propylene and butylene or mixtures thereof.

The chain of phase B may also include sections of a different kind, such as isoprene, butadiene or similar substances, for example. It is also possible for polystyrene blocks to be present in the soft phase B, in amounts of up to 20% by weight. The overall styrene content is always lower than 65% by weight, preferably less than 40% by weight, with particular preference from 3 to 35% by weight. Preference is given to styrene contents of between 3% by weight and 35% by weight, since a lower styrene content makes the cold seal composition more conforming.

The sum of the weight fractions of the block copolymers in the cold seal composition is preferably more than 20% by weight, more preferably more than 30% by weight, with particular preference from 30 to 70% by weight, and most preferably from 50 to 70% by weight. The controlled blending of diblock and triblock copolymers is especially advantageous, preference being given to a diblock copolymer content of less than 80% by weight.

Very particularly, the blend of block copolymers based on SEPS and SEBS is notable for its diverse possibilities for variation. Particular variations of the two polymer types are advantageous in a ratio of from 1:100 to 100:1, preferably from 1:10 to 10:1, with particular preference from 1:3 to 3:1. By way of example, different A/B diblock copolymers of the SEBS may be combined with different A/B/A triblock copolymers of the SEPS. A combination of different A/B diblock copolymers of the SEPS with different A/B/A triblock copolymers of the SEBS is likewise possible. Also possible, furthermore, is the combination of different A/B/A triblock copolymers of the SEPS with different A/B/A triblock copolymers of the SEBS. For some applications, advantages have been found from compounding A/B diblock copolymers of SEBS and of SEPS. In a first advantageous embodiment, the cold seal composition comprises one or more A/B diblock copolymer types based on SEPS and at least one A/B/A triblock copolymer type based on SEBS. In a further advantageous embodiment, the cold seal composition comprises one or more A/B diblock copolymer types based on SEBS and at least one A/B/A triblock copolymer type based on SEPS. In a further advantageous embodiment, the cold seal composition comprises one or more A/B/A triblock copolymer types based on SEPS and at least one A/B/A triblock copolymer type based on SEBS.

In one advantageous embodiment, the latex-free cold seal composition is made up as indicated below:

| | |
|---|---|
| from 5 to 90% by weight of | block copolymers, |
| from 5 to 80% by weight of | tackifiers such as oils, waxes, resins and/or mixtures thereof, preferably mixtures of resins and oils, |
| less than 60% by weight of | plasticizers, |
| less than 15% by weight of | additives, |
| less than 5% by weight of | stabilizers. |

The aliphatic or aromatic oils, waxes, and resins used as tackifiers are preferably hydrocarbon oils, waxes, and resins, the consistency of the oils (such as paraffinic hydrocarbon oils) or of the waxes (such as paraffinic hydrocarbon waxes) giving them a favorable effect on sticking activity. In one specific embodiment, the cold seal composition comprises at least one aliphatic hydrocarbon resin and at least one aromatic hydrocarbon resin. Plasticizers used include medium- or long-chain fatty acids and/or their esters. These additions serve to set the sticking properties and the stability. Where appropriate, further stabilizers and other auxiliaries are employed. Filling the cold seal composition with mineral fillers, fibers or solid or hollow microbeads is possible.

The cold seal compositions are preferably formulated such that at a frequency of 0.1 rad/s they have a dynamic-complex glass transition temperature of less than −30° C., preferably of less than −50° C., with very particular preference from −55° C. to 150° C.

Stringent requirements in respect of the sticking properties are imposed in particular on orthopedic dressings and bandages. For ideal use, the cold seal composition should not exhibit any tack. Furthermore, so that there is no slipping, the cold seal composition needs to have a high shear strength. Through the controlled reduction in the glass transition temperature of the cold seal composition, which is a consequence of the selection of the tackifiers, of the plasticizers, and of the polymer molecule size and molecular distribution of the starting components, the required, functionally appropriate sticking of the composition to itself, i.e., to the reverse of the backing of the sheet material, is achieved. The high shear strength of the cold seal composition employed here is achieved through the high cohesiveness of the block copolymer. The low tack is a result of the range of tackifiers and plasticizers that is used in combination with the block copolymer.

Product properties such as tack and shear stability may be quantified readily by means of a dynamomechanical frequency measurement. This is done using a rheometer controlled by shearing stress. The results of this measurement method give information on the physical properties of a substance by taking into account the viscoelastic component. At a specified temperature, the cold seal composition is set in oscillation between two plane-parallel plates at variable frequencies and with low deformation (linear viscoelastic region). Via a pickup control unit and with computer assistance, the quotient (Q=tan δ) between the loss modulus (G", viscous component) and the storage modulus (G', elastic component) is determined.

$$Q = \tan \delta = G''/G'$$

A high frequency is chosen for the subjective sensing of the tack, and a low frequency for the shear strength. A low numerical value denotes low tack and good shear stability.

| Designation | Shear strength low frequency/RT | Tack high frequency/RT |
|---|---|---|
| Cold seal composition A | tan δ = 0.08 ± 0.03 | tan δ = 0.24 ± 0.03 |
| Cold seal composition B | tan δ = 0.32 ± 0.03 | tan δ = 0.15 ± 0.03 |

In cold seal compositions of the invention, the ratio of the viscous component to the elastic component at a frequency of 100 rad/s and 25° C. is less than 0.4, in particular from 0.02 to 0.37, and then from 0.04 to 0.28. Preferably, the cold seal compositions have a ratio of the viscous component to the elastic component at a frequency of 0.1 rad/s and 25° C. of less than 0.5, more preferably between 0.35 and 0.02, with very particular preference between 0.3 and 0.05.

As a preferred process for producing an open-pored, cohesive, air and water vapor permeable coating of the cold seal composition on the backing material it is possible to employ the spinning technology for applying thermoplastics and adhesives.

The contactless coating and application of cold seal compositions in hotmelt form by spinning or spraying with compressed air or inert gases has already been widely and successfully used.

With stringent requirements on uniformity and low weight per unit area, however, the limits for coating at high viscosities are narrow. Particularly when applying adhesives with a relatively high viscosity of more than 10 Pa*s, a tendency toward severe "blobbing" appears. On the basis of fundamental scientific research into spraying jet theory, therefore, special spraying techniques have been developed for thermoplastics of relatively high viscosity (high molecular mass).

Using the melt spin, Acufiber and Durafiber processes, it is nowadays possible to process thermoplastics in the pressure-sensitive sector at up to 2000 Pa*s at 200° C. Accordingly, a range of application possibilities in the sector of the spraying of thermoplastic adhesives becomes possible.

The advantages of this application technique, such as contactless coating, independent of geometry, coupled with low thermal loading of the backings, opens up access to completely new dressing specialties.

The multiplicity of techniques are described, by way of example, by Acumeter, J+M Laboratories, Dynafiber, and ITO Dynatex Nordson. Common to all of them are the flow processes in the spray nozzles. Melted thermoplastics are among the group of nonnewtonian liquids with a pseudoplastic rheology, i.e., shearing stress and coating speed are not in linear correlation with one another. The thermoplastic polymers most commonly used as hotmelt adhesives consist of linear and/or branched chain molecules. In the course of the process of aerodynamic stretching, the flow rate increases at the sprayed filament and the molecules become more and more disentangled and orient themselves in the flow direction.

For this reason, all nozzles utilize an internal mixing principle in which the adhesives are surrounded by a flow of compressed air while still within the nozzle chamber. The narrowest gap is therefore the nozzle outlet. The outlet gap may be circular or slot-shaped. If this spray filament is sprayed onto a substrate, the result is a random-laid nonwoven with an intrinsically linked structure. The random-laid nonwoven consists of a disordered, homogeneous arrangement of a looped continuous filament.

The coat which is applied contactlessly via an arbitrary series of nozzles, dependent on the coating width, and is spun in a weblike manner possesses a free surface area which is many times greater than that of full-area coatings.

Additionally, the spinning technique likewise offers a number of technical process possibilities for the use of partial coatings for cold seal compositions.

A further possibility is to carry out spinning onto, or around, constituents of the sheet material. For example, spinning may have been carried out around the threads of a woven or knit, so that actual coating takes place on one side only and yet a good assembly of plies is able to develop.

A modified, functionally appropriate use of the sheet material is achieved through the foaming of the cold seal compositions.

The cold seal compositions to be used are in this case foamed preferably using inert gases such as nitrogen, carbon dioxide, noble gases, hydrocarbons or air, or mixtures thereof. In some cases, foaming additionally by thermal decomposition of gas-evolving substances such as azo, carbonate, and hydrazide compounds has proven suitable.

The degree of foaming, i.e., the gas content, should be at least about 5% by volume and may reach up to about 85% by volume. In practice, values from 10% by volume to 75% by volume, preferably 50% by volume, are well established. Operating at relatively high temperatures of approximately 100° C. and a comparatively high internal pressure produces very open-pored foam layers whose permeability to air and water vapor is particularly good. The advantageous properties of the system are its good conformability, even to uneven surfaces, owing to the elasticity and plasticity of the foamed device.

One particularly suitable process for preparing the cold seal compositions foamed in accordance with the invention operates in accordance with the foam-mix system. In this system, the thermoplastic cold seal composition is reacted with the gases provided, such as nitrogen, air or carbon dioxide, for example, in various volume fractions (from about 10% by volume to 80% by volume) in a stator/rotor system under high pressure and at a temperature above the softening point (approximately 120° C.). While the gas entry pressure is greater than 100 bar, the mixing pressures between gas and thermoplastic in the system are from 40 to 100 bar, preferably from 40 to 70 bar. The cold seal foam prepared in this way is then able to pass through a line into the applicator unit. In the applicator unit, commercial nozzles, extruder systems or chamber systems are used. As a result of the foaming of the device and the open pores which it produces in the composition, the products coated with this device are, given the use of an inherently porous backing, of good water vapor and air permeability. The amount required for sticking is considerably reduced without detriment to the mode of action and the properties.

It is further advantageous, especially for use in the case of medical products, if the composition is applied partially to the backing material, by means for example of halftone printing, thermal screen printing, thermal flexographic printing or gravure printing, since backing materials which have been given a self-adhesive coating in a continuous applied line may under unfavorable conditions, during application, induce instances of mechanical skin irritation.

The partial application makes it possible for the transepidermal water loss to be dissipated through regulated channels, and improves the evaporation of perspiration from the skin, especially when the backing materials used are permeable to air and water vapor. This prevents instances of skin irritation due to accumulation of body fluids. The dissipation channels employed allow said fluids to be conducted away.

Preference is given to application in the form of polygeometric domes and, very particularly, of domes where the ratio of diameter to height is less than 5:1. Printed application of other shapes and patterns on the backing material is also possible; for example, a printed image in the form of alphanumeric character combinations or patterns such as lattices, stripes, and zigzag lines. The cold seal composition may be distributed uniformly over the backing material; alternatively, it may be applied with a thickness or density which varies over the area, as is appropriate to the function of the product.

The principle of thermal screen printing consists in the use of a rotating, heated, seamless, drum-shaped, perforated, cylindrical screen which is fed via a nozzle with the preferred composition. A specially shaped nozzle lip (circular or square bar) presses the composition, which is fed in via a channel, through the perforation of the screen wall and onto the backing web that is conveyed past it. This web is guided by means of a counterpressure roller against the external jacket of the heated screen drum, at a speed which corresponds to the peripheral speed of the rotating screen drum.

The small domes are formed in accordance with the following mechanism: The pressure of the nozzle bar conveys the composition through the screen perforation onto the backing material. The size of the domes formed is determined by the diameter of the screen perforation. The screen is lifted from the backing in accordance with the traveling speed of the backing web (rotation speed of the screen drum). As a consequence of the adhesion of the cold seal composition in the melt and the internal cohesion of the hotmelt, the limited supply of hotmelt composition in the perforations is drawn in sharp definition from the base of the dome that is already adhering to the backing, and is conveyed onto the backing by the pressure of the bar. After the end of this travel, the more or less strongly curved surface of the dome forms over the specified base area in dependence on the rheology of the hotmelt composition. The height-to-base ratio of the dome depends on the ratio of the perforation diameter to the wall thickness of the screen drum and on the physical properties (rheology, surface tension, and contact angle on the backing material) of the cold seal composition.

For the screen in thermal screen printing, the web-to-hole ratio may be less than 10:1, preferably less than or equal to 1:1, and in particular equal to 1:10.

The mechanism of dome formation described preferentially requires backing materials that are absorbent or are at least wettable by the cohesive composition. Nonwetting backing surfaces have to be pretreated by chemical or physical processes. This may be done by means of additional measures such as corona discharge, for example, or coating with substances which improve wetting.

Using the printing process indicated, it is possible to lay down the size and shape of the domes in a defined manner. The bond strength values which are relevant for the application, and which determine the quality of the products produced, are within very narrow tolerances when coating is carried out properly. The base diameter of the domes may be selected to be from 10 μm to 5 000 μm and the height of the domes from 20 μm to about 2000 μm, preferably from 50 μm to 1000 μm, the low-diameter range being intended for smooth backings and the range of greater diameter and greater dome height being intended for rough or highly porous backing materials. The positioning of the domes on the backing is laid down in a defined manner by the geometry of the applicator unit—for example, the gravure geometry or screen geometry—which can be varied within wide limits. With the aid of the parameters indicated, it is possible, by way of adjustable variables, to set with very great precision the desired profile of properties of the coating, harmonized with the various backing materials and applications.

The backing material is preferably coated at a speed of more than 2 m/min, preferably from 20 to 220 m/min, at a temperature chosen so as to be greater than the softening temperature.

The cohesive composition may be applied to the backing material with a coating weight of more than 3 $g/m^2$, preferably between 6 $g/m^2$ and 180 $g/m^2$, with particular preference between 9 g/m2 and 140 $g/m^2$, with very particular preference between 9 $g/m^2$ and 50 $g/m^2$.

The percentage of the area that is coated with the cold seal composition should be at least 10% and may reach up to approximately 95%, for specific products preferably from 40% to 60% and also from 70% to 95%. This may be achieved, where appropriate, by multiple application or special deformation steps, in which case it is also possible, if desired, to use compositions having different properties.

The combination of the cold seal compositions and the partial coating on the one hand ensures reliable binding of the medical product to itself; on the other hand, allergic or mechanical skin irritations, at least those which are perceptible visually, are ruled out, even in the case of use extending over a number of days. Moreover, large domes are found to exert a massaging effect.

Depending on the backing material and its temperature sensitivity, the composition may be applied directly or may be applied first to an auxiliary support and then to the ultimate backing. Additionally, subsequent calendering of the coated product and/or pretreatment of the backing, such as corona irradiation, may be advantageous for better anchoring of the sticking coat. Furthermore, treatment of the composition with electron beam postcrosslinking, or UV irradiation, may result in an improvement in the desired properties.

It is likewise within the inventive concept to coat the backing material on two sides. Suitable backing materials include all rigid and elastic sheet materials of synthetic and natural raw materials. Preference is given to backing materials which, following application of the cold seal composition, could be employed in such a way that they possess the characteristics of a functionally appropriate dressing.

Specifically for orthopedic applications, the materials ought to have an ultimate tensile stress strength of more than 1000 cN/cm, preferably from 2000 cN/cm to 22000 cN/cm, in order to give functionally appropriate support.

Furthermore, the ultimate tensile stress elongation of the backing materials under a load of 10 N/cm should be less than 300%, in particular less than 30%. For long-stretch bandages, the range from 150% to 250% is preferred. In the case of short-stretch and medium-stretch bandages, a range from 50 to 150% is advantageous, and for stretch underwraps and dressing materials the stretching range is from 5% to 100%.

Backing materials used include, in particular, textiles such as wovens, knits, lays, nonwovens, laminates, nets, and also films, foams, and papers. Furthermore, these materials may be pretreated and/or aftertreated. Common pretreatments include corona and water repellency treatment; customary aftertreatments include calendering, heat treatment, laminating, punching, and enveloping.

The backing material coated with the composition may have an air permeability of more than 1 $cm^3/(cm^2 \times s)$, in particular more than 70 $cm^3/(cm^2 \times s)$, preferably from 5 $cm^3/(cm^2 \times s)$ to 200 $cm^3/(cm^2 \times s)$, with very particular preference from 15 $cm^3/(cm^2 \times s)$ to 120 $cm^3/(cm^2 \times s)$, and also a water vapor permeability of more than 500 $g/(m^2 \times 24\ h)$, preferably from 770 $g/(m^2 \times 24\ h)$ to 5 100 $g/(m^2 \times 24\ h)$, with particular preference from 990 $g/(24\ h \times m^2)$ to 3000 $g/(24\ h \times m^2)$.

Finally, following the coating operation, the device may be enveloped in a backing material which repels adhesive, such as siliconized paper, or may be provided with a wound contact material or padding. Subsequently, the devices are punched out in the desired size. It is particularly advantageous that the device is sterilized, preferably by means of γ (gamma) radiation. This is particularly suitable for subsequent sterilization of a block copolymer-based system containing no double bonds. It applies in particular to the preferred styrene-propylene-ethylene-styrene and styrene-ethylene-butylene block copolymer. This procedure is not accompanied by any application-significant changes in the properties.

A further advantage of the fully hydrogenated polymers and additives is the high light fastness. In the unfilled state it is possible to produce compounds ranging from clear to only slightly yellowish, with a Hazen number of less than 3, preferably from 0 to 2. The Hazen (color) number (after the American water engineer A. Hazen) is the number of mg of platinum [as potassium hexachloroplatinate(IV), dissolved 1.246:1 with cobalt(II) chloride hexahydrate in 1000 ml aqueous hydrochloric acid] which, at the same coat thickness, have (approximately) the same color as the sample (source: Römpp Lexikon Chemie—Version 1.3, Stuttgart/New York: Georg Thieme Verlag 1997).

The device of the invention may have a bond strength to the reverse of the backing of at least 0.2 N/cm, in particular a bond strength of between 0.3 N/cm and 5N/cm, with particular preference between 0.4 N/cm and 3.0 N/cm. The bond strengths achieved to other substrates are as good as zero. On the skin in particular, bond strengths of less than 0.3 N/cm are found.

The sticking values (sticking side to sticking side) at a 180° C. angle of the sample coatings on a polyester film were, for example, 22 cN/cm for the cold seal composition A (see table above) at a coating weight of 20 $g/m^2$ and 37 cN/cm for the cold seal composition B at a coating weight of 18 $g/cm^2$.

In the text below, advantageous backing materials of the invention are disclosed, together with their properties.

Backing Material A

The backing material coated with cold seal composition has an air permeability of more than 15 cm³/(cm²×s) and a water vapor permeability of more than 500 g/(24 h×s).

The cold seal composition comprises one or more SEBS and/or SEPS triblock copolymer type(s).

The sum of the weight percentages of all block copolymers in the cold seal composition is from 30% by weight to 70% by weight.

The cold seal composition comprises an aliphatic and an aromatic hydrocarbon resin.

The backing material has a cold seal composition coating weight of from 6 to 180 g/m².

The Hazen number is less than 3.

Backing Material B

The backing material coated with cold seal composition has an air permeability of more than 15 cm³/(cm²×s) and a water vapor permeability of more than 500 g/(24 h×s).

The cold seal composition comprises one or more SEPS and/or SEBS triblock copolymer type(s).

The sum of the weight percentages of all block copolymers in the cold seal composition is from 30% by weight to 70% by weight.

The cold seal composition comprises an aliphatic and an aromatic hydrocarbon resin.

The backing material has a cold seal composition coating weight of from 6 to 180 g/m².

The Hazen number is less than 3.

The backing material is suitable especially for medical products, particularly plaster, medical fixations, wound coverings, orthopedic or phlebological bandages, and dressings. Furthermore, however, the backing material may be used for reversible technical fixations which can be undone without damage to the substrate.

In the text below, a number of figures will be used to illustrate means of producing backing materials of the invention.

In the simplest case, according to FIG. 1, the means consist of an unwinder (1) and a winder (2) and also the backing web (4) and the spinning nozzle (3).

Figure 2:
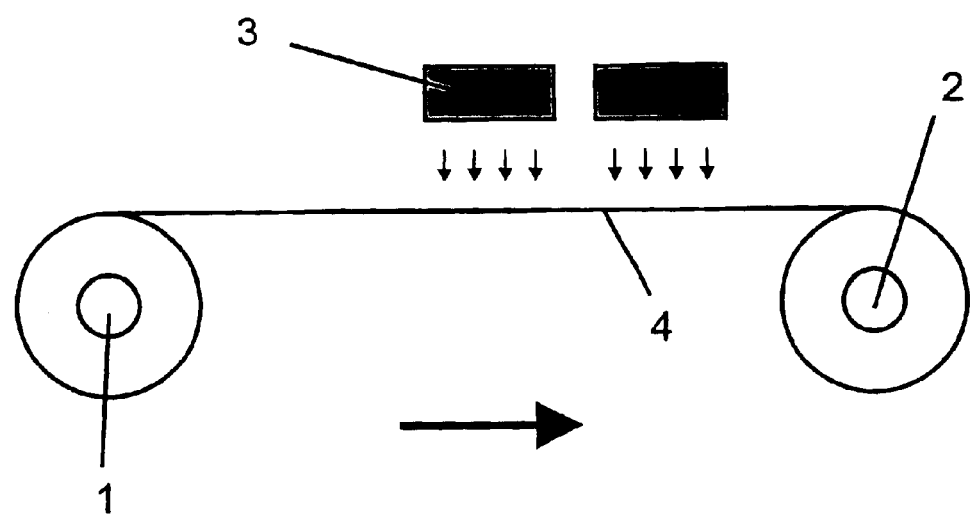

In order to optimize the properties, it is also possible to place a plurality of nozzles (3) in series, as in FIG. 2.

Figure 3:
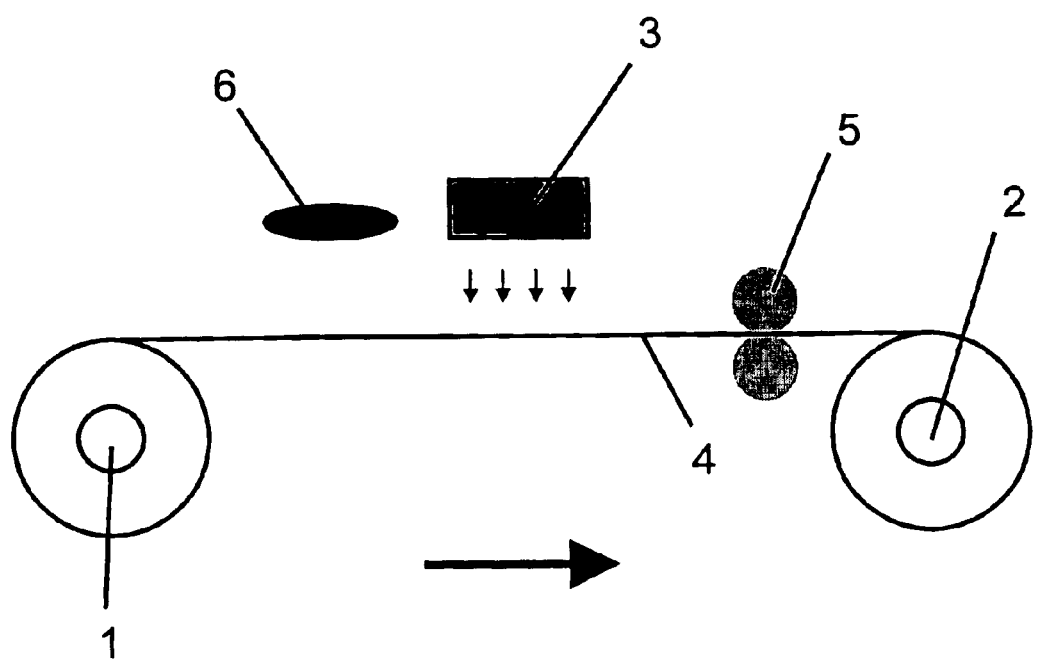

For specific backings, a corona pretreatment (6) or downstream calendering station may be included in the experimental setup, as shown in FIG. 3. Further, it is possible to treat the coated sides of the backing material differently. A combination of a spun cold seal composition with a partial pointwise coating may be advantageous. The cold seal compositions on the different sides may, where appropriate, also be different. One particular embodiment features an SEBS cold seal composition on one side, while the other side contains an SEPS-based cold seal composition.

In the text below, examples of the invention will be described, without wishing thereby to restrict the invention unnecessarily.

EXAMPLE 1

In accordance with the invention, a dressing which sticks to itself was produced, on both sides of which a cold seal composition was applied by spinning. On the basis of its properties, described below, the dressing may serve for use as an undermaterial for support dressings, which because of the medical indications may have to be applied for several days to joints of the human locomotor system. The backing material consisted of an inelastic cotton fabric having an ultimate tensile stress strength of more than 15 N/cm and an ultimate tensile stress elongation of less than 40%.

The makeup of this cold seal composition was as follows:

an SEPS block copolymer comprising hard and soft segments and having a styrene content in the polymer of 13 mol %; its proportion in the composition was 65% by weight (Kuraray Co.)

a paraffinic hydrocarbon resin, with a proportion in the composition of 34% by weight an aging inhibitor, with a proportion of less than 1.0% by weight (Irganox 1010, Ciba)

The components employed were homogenized in a thermal mixer at 185° C. for 3.5 h. The softening point of this cold seal composition was approximately 85° C. (DIN 52011), and it had a viscosity of 2100 mPas at 175° C. (DIN 53018, Brookfield DV II, sp. 21). The glass transition temperature by the method referred to above was less than −50° C. The cold seal composition was spun with a nozzle and applied two-dimensionally to the backing. The direct, double-sided coating was carried out at 20 m/min and a temperature of 130° C. The backing material was coated with 22 g/m².

Bond strengths of 0.6 N/cm for the material to itself were found. Sticking to the skin was not observed.

EXAMPLE 2

This example describes a three-ply nonwoven with a flexible middle layer made of polypropylene and two outer plies, which comprise the cold seal composition. The ultimate tensile stress strength of the sheet material after solidification was 25 N/cm, the ultimate tensile stress elongation 48%. The weight per unit area of the middle layer was 33 g/m², that of the outer plies 17 and 5 g/m².

The makeup of the cold seal composition was as follows:

| | |
|---|---|
| an SEPS block copolymer (Septon 2002, Kuraray) | 100 |
| an aromatic hydrocarbon resin (Kristalex F85, Hercules) | 38 |
| an aliphatic hydrocarbon resin (Escorez 5380, Exxon) | 38 |
| a mineral oil (Odina G33) | 75 |
| Irganox 1010 | 2 |

The cold seal composition was homogenized in a thermal mixer at 185° C. The tan δ of the cold seal composition at 25° C. and a frequency of 100 rad/s was 0.14. The cold seal composition was spun using a nozzle and applied two-dimensionally to the backing. The direct, two-dimensional coating was carried out with a web speed of 35 m/min at a temperature of 137° C. The bond strength was found to be 13 cN/cm.

EXAMPLE 3

Example 3 discloses a dressing for orthopedic use. An elastic woven fabric based on a cotton/elastane blend was used. In the unstretched state, the fabric had a basis weight of 150 g/m². The number of warp threads was 14/cm. The fabric was constructed such that the elastomer thread, which was wrapped with two cotton threads, was followed by four crimped cotton threads. The ultimate tensile strength of the sheet material after solidification was 23 N/cm and the ultimate tensile stress elongation was 130%.

The makeup of the cold seal composition was as follows:

| | |
|---|---|
| an SEBS block copolymer (Kraton G 1652, Shell) | 59.8 |
| an aromatic hydrocarbon resin (Kristalex F85, Hercules) | 4.8 |
| an aliphatic hydrocarbon resin (Escorez 5380, Exxon) | 4.9 |
| a mineral oil (Pioneer 2071, Hansen & Rosenthal) | 29.9 |
| Irganox 1010 | 0.6 |

The cold seal composition was homogenized in a thermal mixer at 185° C. The tan δ of the cold seal composition at 25° C. and a frequency of 100 rad/s was 0.05. The cold seal composition was applied partially to the backing by means of thermal screen printing, using a 60 mesh/200 μm screen from Stork. The coating was carried out with a web speed of 35 m/min at a temperature of 137° C. The bond strength was found to be 0.63 cN/cm.

EXAMPLE 4

This example discloses a dressing for phlebological use. An elastic woven fabric based on twisted cotton threads was used. In the unstretched state, the fabric had a basis weight of 300/m². The number of warp threads was 17/cm. The ultimate tensile strength of the sheet material after solidification was 120 N/cm and the ultimate tensile stress elongation was 110%.

The makeup of the cold seal composition was as follows:

| | |
|---|---|
| an SEBS block copolymer (Kraton G 1652, Shell) | 100 |
| an aromatic hydrocarbon resin (Kristalex F85, Hercules) | 28 |
| an aliphatic hydrocarbon resin (Escorez 5380, Exxon) | 12 |
| a mineral oil (Pioneer 2071, Hansen & Rosenthal) | 60 |
| Irganox 1010 | 2 |

The cold seal composition was homogenized in a thermal mixer at 175° C. The tan δ of the cold seal composition at 25° C. and a frequency of 100 rad/s was 0.05. The cold seal composition was foamed using a foam generator (from Nordson) and applied over the full area of the backing, producing a coating of irregular appearance. The degree of foaming of the cold seal composition was 48%. The coating was carried out with a web speed of 5 m/min at a temperature of 141° C. The bond strength was found to be 0.83 cN/cm. Sticking to the skin was not found. The dressing exhibited an air permeability of 26 cm³/(cm²×s).

EXAMPLE 5

For a special fixation dressing, a very open gauze was coated. The ultimate tensile stress strength of the sheet material after solidification was 13 N/cm, the ultimate tensile stress elongation 21%. The basis weight of the gauze was 32 g/m².

The makeup of the cold seal composition was as follows:

| | |
|---|---|
| an SEBS block copolymer (Kraton G 1652, Shell) | 100 |
| an aromatic hydrocarbon resin (Kristalex F85, Hercules) | 28 |
| an aliphatic hydrocarbon resin (Escorez 5380, Exxon) | 12 |
| a mineral oil (Pioneer 2076, Hansen & Rosenthal) | 60 |
| Irganox 1010 | 2 |

The cold seal composition was homogenized in a thermal mixer at 180° C. The tan δ of the cold seal composition at 25° C. and a frequency of 100 rad/s was 0.05. The cold seal composition was spun using a nozzle and applied two-dimensionally to the backing at 20 g/m² per side. The direct, two-dimensional coating was carried out with a web speed 35 m/min at a temperature of 137° C. The bond strength was found to be 63 cN/cm.

What is claimed is:

1. A medical article comprising:
   a) a backing material; and
   b) a latex-free, cold seal composition applied to one or both sides of the backing material;
   wherein:
   i) the cold seal composition is a pressure sensitive adhesive having an ultimate tensile stress strength of at least 800 cN/cm;
   ii) the cold seal composition comprises one or more block copolymers having a styrene content of less than 65% by weight; and
   iii) the cold seal composition has a tan δ of less than 0.4 at a temperature of 25° C. and a frequency of 100 rad/s, wherein tan δ is a quotient between a loss modulus and a storage modulus, and
   iv) individual plies or turns of the medical article adhere to other plies or turns of the medical article, but not substantially to a substrate selected from the group consisting of skin, hair and clothing.

2. The medical article as claimed in claim 1, wherein the cold seal composition is constructed on a block copolymer basis.

3. The medical article as claimed in claim 2, wherein the block copolymer is A-B or A-B-A block copolymers or mixtures thereof.

4. The medical article as claimed in claim 1, wherein the overall styrene content in the polymer is less than 40% by weight.

5. The medical article as claimed in claim 1, wherein the cold seal composition has a dynamic-complex glass transition temperature at a frequency of 0.1 rad/s of less than −30° C.

6. The medical article as claimed in claim 5, wherein the dynamic-complex glass transition temperature is less than −50° C.

7. The medical article as claimed in claim 5, wherein the dynamic-complex glass transition temperature is from −55° C. to 150° C.

8. The medical article as claimed in claim 1, wherein the cold seal composition is applied partially and/or foamed with an inert gas.

9. The medical article as claimed in claim 1, wherein the cold seal composition is applied to the backing material by a printing process selected from the group consisting half-tone printing, thermal screen printing and gravure printing.

10. The medical article as claimed in claim 1, wherein the cold seal composition is applied to the backing material in the form of polygeometric domes.

11. The medical article as claimed in claim 1, wherein the cold seal composition is coated on the backing material with a coating weight of more than 3 g/m².

12. The medical article as claimed in claim 1, wherein the ultimate tensile stress elongation of the backing material is less than 300% and/or the ultimate tensile stress strength is from 1000 to 22000 cN/cm.

13. The medical article as claimed in claim 12, wherein the ultimate tensile stress elongation of the backing material is from 5 to 100%, and/or the ultimate tensile stress strength is from 1000 and 22000 cN/cm.

14. The medical article as claimed in claim 12, wherein the ultimate tensile stress elongation of the backing material is from 150% to 250%, and/or the ultimate tensile stress strength is from 1000 to 22000 cN/cm.

15. The medical article as claimed in claim 12, wherein the ultimate tensile stress elongation of the backing material is less than 30%, and/or the ultimate tensile stress strengths is from 1000 to 22000 cN/cm.

16. The medical article as claimed in claim 1, wherein the bond strength of the coated backing material is between 0.4 N/cm and 3.0 N/cm.

17. The medical article as claimed in claim 1, wherein the medical article is enveloped or is provided with a wound contact material or padding.

18. The medical article as claimed in claim 1, wherein the medical article is sterilized.

19. The medical article as claimed in claim 3, wherein phase A is polystyrene or its derivatives and phase B is at least one member selected from the group consisting of ethylene, propylene, butylene, butadiene, isoprene and mixtures thereof.

20. The medical article as claimed in claim 19, wherein phase B is selected from at least member selected from the group consisting of ethylene, propylene and butylene and mixtures thereof.

21. The medical article as claimed in claim 1, wherein the overall styrene content in the polymer is from 3 to 35% by weight.

22. The medical article as claimed in claim 1, wherein the cold seal composition is coated on the backing material with a coating weight of between 6 g/m$^2$ and 180 g/m$^2$.

23. The medical article as claimed in claim 1, wherein the cold seal composition is coated on the backing material with a coating weight of between 9 g/m$^2$ and 140 g/m$^2$.

24. A method of using a medical article as claimed in claim 1 in a medical treatment of a patient, said method comprising wrapping said medical article around a portion of a body of a patient receiving said medical treatment.

25. The method as claimed in claim 24, wherein the medical article is in the form of a medical product selected from the group consisting of plasters, medical fixations, would coverings, orthopedic or phlebological bandages, and dressings.

26. A method of using a medical article as claimed in claim 1, comprising wrapping said medical article around a substrate, and optionally removing said medical article from around said substrate without damaging the substrate.

* * * * *

UNITED STATES PATENT AND TRADEMARK OFFICE
CERTIFICATE OF CORRECTION

PATENT NO. : 6,812,170 B1
APPLICATION NO. : 10/009147
DATED : November 2, 2004
INVENTOR(S) : P. Himmelsbach et al.

It is certified that error appears in the above-identified patent and that said Letters Patent is hereby corrected as shown below:

Column 12, Line 65, "from 1000 and 22000 cN/cm" should read -- from 1000 to 22000 cN/cm --

Column 13, Line 5, "strengths" should read -- strength --

Column 14, Line 16, "would coverings" should read -- wound coverings --

Signed and Sealed this

Tenth Day of July, 2007

JON W. DUDAS
*Director of the United States Patent and Trademark Office*